United States Patent [19]
Baldwin et al.

[11] Patent Number: 6,043,371
[45] Date of Patent: Mar. 28, 2000

[54] ORGANIC COMPOUND SYNTHESIS

[76] Inventors: Jack Edward Baldwin, Broom, Hinksey Hill, Oxford, OX1 5BH; Robert Michael Adlington, 5 Colegrove Down, Oxford, OX2 9HT; Nicholas Paul Crouch, Reed Place Farmhouse, Chainhurst, Marden, Nr Tonbridge, Kent, TN12 9SU, all of United Kingdom

[21] Appl. No.: 09/131,200

[22] Filed: Aug. 7, 1998

[30] Foreign Application Priority Data

Aug. 12, 1997 [GB] United Kingdom ............ 9717107

[51] Int. Cl.$^7$ .............................................. C07D 211/94
[52] U.S. Cl. ........................................ 546/301; 546/273.7
[58] Field of Search ........................................ 546/301

[56] References Cited

U.S. PATENT DOCUMENTS

| 5,616,713 | 4/1997 | Chou et al. | 546/250 |
|---|---|---|---|
| 5,625,069 | 4/1997 | Chou et al. | 546/250 |

FOREIGN PATENT DOCUMENTS

| 0 484 265 | 5/1992 | European Pat. Off. |
|---|---|---|
| WO98/50361 | 11/1998 | WIPO |

OTHER PUBLICATIONS

*Chemical Abstracts*, 107(5), 702, abstract No. 39810s (abstract of ES 543 816) (1986).
*Chemical Abstracts*, 108(15), 758, abstract No. 131819v (abstract of ES 550 070) (1987).
S.–Y. Chou et al., *Heterocycles*, 45(1), 77–85 (1997).
*Patent Abstracts of Japan*, 17(391) (abstract of JP 5–070432) (1993).
*Patent Abstracts of Japan*, 12(62) (abstract of JP 63–183577) (1988).

*Primary Examiner*—Jane Fan
*Attorney, Agent, or Firm*—Wenderoth, Lind & Ponack, L.L.P.

[57] ABSTRACT

A strategy for synthesising omeprazole 10 starting from compound 1 as shown in the diagram. Individual method steps 1→2, 2→3, 3→4, 4→5, 5→6, 6→7, and intermediate compounds 2, 3, 4, 5, 6 and 9 are also claimed as new.

4 Claims, No Drawings

ORGANIC COMPOUND SYNTHESIS

Omeprazole is one of the world's leading pharmaceutical products. The drug inhibits gastric acid secretion. It is a specific inhibitor of the gastric proton pump $(H^++K^+)$-ATPase. Various synthetic routes to Omeprazole are described in the following patent specifications: EP 5129; EP 103553; EP 124495; EP 484265; U.S. Pat. Nos. 4,255,431; 5,066,810; 5,616,713; 5,625,069. Many of the synthetic methods described involve use of 2,3,5-trimethylpyridine N-oxide and/or 2,3,5-trimethylpyridine. Literature methods exist for synthesis of these compounds from 3,5-dimethylpyridine, but which involve the use of strong and potentially dangerous bases. Likewise, pyridine N-oxides are recognised as being toxic.

The present invention is concerned with the preparation of Omeprazole 10 by a new synthetic strategy which is outlined in the reaction scheme. Several of the intermediate compounds shown in the scheme are new and form part of this invention. Several individual reaction steps, as well as the overall synthesis, are new and form part of this invention. The overall method has several advantages. The intermediates are generally not toxic, or at least less toxic than intermediates used in prior synthetic routes. Many of the intermediates are crystalline compounds that are readily recovered and purified. Many of the reactions go easily to give high yields of the desired compounds.

The compound of formula 1 is described for example in Organic Syntheses, 1992, 70, 231.

The invention provides a method of making a compound of formula 2, where L is N-pyrrolidino or N-morpholino, which method comprises reacting a compound of formula 1 with pyrrolidine or morpholine. As solvent, preferably benzene or toluene is used.

The invention also provides a compound having formula 2, where L is N-pyrrolidino or N-morpholino.

The invention also provides a method of making a compound of formula 3, where R is $C_1$–$C_6$ alkyl, which method comprises reacting a compound of formula 2, where L is a cyclic or acyclic disubstituted amino group, with oxalyl chloride or oxalyl bromide and a $C_1$–$C_6$ alkanol. This is a key step of the method. The secondary amine is preferably either a di($C_1$–$C_6$)alkyl amine, or a cyclic amine e.g. piperidine, morpholine, hexamethyleneimine, or particularly pyrrolidine. Preferably 2 to 5 equivalents, particularly 3.5 to 4.5 equivalents, of the oxalyl halide are used. Preferred solvents are haloalkanes, including dichloromethane, chloroform, 1,2-dichloroethane, lower alkyl acetates, lower alkyl ketones, is lower dialkyl ethers and mixtures thereof. A lower alkanol is used as a quenching agent. An advantage of using ethanol rather than methanol is that diethyloxalate, formed as a by-product, is a liquid and easily removed.

The invention also provides a compound having formula 3, where R is methyl or $C_3$–$C_6$ alkyl.

The invention also provides a method of making a compound of formula 4, which method comprises reacting a compound of formula 3 with a suitable hydride-donor reducing agent. It is rather surprising that this reaction goes well with minimal side-reactions, especially when using sodium borohydride as esters usually reduce only very slowly under such conditions. Preferred reducing agents are alkali metal borohydrides, alkali metal hydroaluminates, and other hydride-donors, e.g. sodium borohydride, sodium cyanoborohydride, lithium borohydride, lithium alkylhydroaluminates, lithium alkylborohydrides, diisobutylaluminium hydride, in the presence or absence of a suitable Lewis acid. Preferred solvents are lower alkyl alcohols including methanol and ethanol, lower alkyl acyclic and cyclic ethers, including diethyl ether, tetrahydrofuran, dioxan and 1,2-dimethoxyethane. The reaction goes rapidly at ambient temperature to give a high yield (92% in the example below) of the desired product.

The invention also includes a compound having formula 4. This is a crystalline product, readily made in high yield and readily purified. It is a valuable intermediate in the synthesis of Omeprazole because: the ring oxygen atom can be replaced by nitrogen; and the hydroxymethyl group can be readily activated to allow reaction with substituted 2-mercapto-benzimidazoles such as 5-methoxy-2-mercapto-benzimidazole.

The invention also provides a method of making a compound of formula 5, which method comprises reacting a compound of formula 4 with ammonia. As solvent there may be used either 0.880 ammonia or other aqueous ammonia solution or ammonia in lower alkyl alcohols e.g. methanol or ethanol. The reaction can be performed in a sealed vessel (to avoid evaporation of ammonia) at room temperature or more preferably elevated temperature. The product is recovered as a solid and is dried in order that the next step may be performed under anhydrous conditions.

The invention also includes a compound having formula 5.

The invention also includes a method of making a compound to formula 6, where X is chloro or bromo, which method comprises reacting a compound formula 5 with a chlorinating or brominating agent. Preferably there is used a chlorinating or brominating agent selected from one or more of phosphorous oxychloride, phosphorous pentachloride, triphenylphosphine dichloride, triphenylphosphine dibromide, triphenylphosphite dichloride, triphenylphosphite dibromide, phosphorus tribromide and thionyl chloride, in an appropriate haloalkane solvent e.g. dichloromethane, chloroform, or 1,2-dichloroethane. Preferred conditions are from room temperature to solvent reflux. It is rather surprising that this reaction goes easily in high yield with halogenation taking place at the 2-position as well as the 4-position.

The invention also includes a compound having formula 6 where X is Br.

The invention also includes a method of making a compound of formula 7, where X is bromo, which method comprises reacting a compound of formula 6, where X is bromo, with 5-methoxy-2-mercapto-benzimidazole.

The invention also includes a compound having formula 7, where X is Br.

In order to make a compound of formula 8, a compound of formula 7 may be reacted with a source of methoxide, e.g. an alkali metal methoxide in a suitable solvent. A possible solvent is methanol. Preferred are dipolar aprotic solvents such as dimethyl sulphoxide or 1,3-dimethyl-3,4,5,6-tetrahydro-2-(1H)-pyrimidinone. Reaction temperatures are preferably from ambient to solvent reflux e.g. around 70° C.

The compound of formula 8 may be converted to its hydrochloride salt (9) by reaction with hydrogen chloride or aqueous hydrochloric acid, preferably using as solvent a lower alkyl alcohol e.g. methanol or ethanol. The invention also includes a compound of formula 9. Preferred anti-solvents to aid crystallisation of the compound of formula 9 are lower alkyl acetates e.g. methyl acetate, ethyl acetate etc. and lower dialkyl ethers e.g. diethyl ether. This simplifies purification and isolation of the compound of formula 8. Omeprazole 10 may be made by reacting the compound of formula 8, with an oxidising agent e.g. metachloroperoxybenzoic acid, as described in EP patent 5129.

The invention also includes combinations of the individual steps described herein, including specifically:

a method of making the compound of formula 3 from compound 1 via compound 2;

a method of making the compound of formula 4, from compound 1 via compound 2 and compound 3;

a method of making the compound of formula 6 from compound 4 via compound 5;

a method of making Omeprazole from compound 1 via compounds 2, 3, 4, 5, 6, 7 and 8.

EXPERIMENTAL

DETAILED DESCRIPTION OF THE INVENTION.

Preparation of 2-Methyl-1-penten-1-[N-pyrrolidinyl]-3-one 2. (L=N-pyrrolidino)

To a stirred solution of 2-methyl-1-penten-3-one-1-ol 1 (137g, 1.20 mol) and glacial acetic acid (10 ml) in benzene (400 ml) was added pyrrolidine (170 g, 2.39 mol). The mixture was azeotropically distilled for approximately 5 hours until no more water was liberated. The solvent was evaporated under reduced pressure and the product isolated by vacuum distillation (b.pt. 140–142° C. at 0.35 mmHg) to give 2 (L=N-pyrrolidino) (149.7 g, 75% yield) as an orange/yellow oil which solidified to a waxy solid upon cooling. $^1$H-NMR (CDCl$_3$) δ 1.07 (t, J 7.5 Hz, 3H), 1.86 (m, 4H), 1.93 (s, 3H), 2.48 (q, J 7.5, 2H), 3.51 (m, 4H), 7.38 (s,1H); Ms (APCI+) m/z (%) 168 (MH$^+$, 100).

Preparation of 3,5-Dimethyl-2-methoxycarbonyl-4-pyrone 3. (R=Methyl)

To oxalyl chloride (76.0 g, 0.60 mol) at 0° C., was added in a slow stream with stirring a solution of 2-methyl-1-penten-1-[N-pyrrolidinyl]-3-one 2 (L=N-pyrrolidino) (25.0 g, 150 mmol) in chloroform (20 ml) over a period of 40 minutes. The resulting solution was stirred at reflux for 25 minutes and then evaporated under reduced pressure to give a yellowish brown solid. Xylene (50 ml) was added and the solvent evaporated under vaccuo. Methanol (50mls) was added to the reaction vessel cautiously at room temperature via a reflux condenser, the addition resulting in a strong exotherm and concomitant reflux. After the addition was complete, ca 10 minutes, the resulting solution was refluxed for a further 10 minutes. Activated charcoal (ca 5 g) was added and stirring at reflux continued for a further 5 minutes. The reaction mixture was filtered through celite and then partitioned between diethyl ether (150 ml) and water (150 ml). The aqueous phase was basified to greater than pH 10 with 2M NaOH, the layers separated and the organic phase washed with water (1×50 ml) and 2M HCl (2×50 ml). The etheral layer was dried (anhydrous Na$_2$SO$_4$), filtered and evaporated to give a solid. The solid was dissolved in warm diethyl ether and petroleum ether (80–100° C.) added until crystallisation occurred to give 3. (R=Methyl) A second crop of 3 (R=Methyl) was obtained by concentration of the mother liquors. Crystallisation in this manner gave 3 (R=Methyl) (17.0 g, 62%). m. pt. 70–71° C., $^1$H-NMR (CDCl$_3$) δ 1.96 (s, 3H), 2.31 (s, 3H), 3.95 (s, 3H), 7.73 (s, 1H); Ms (APCI+) m/z (%) 183 (MH$^+$, 100).

Preparation of 3,5-Dimethyl-2-ethoxycarbonyl-4-pyrone 3. (R=Ethyl)

To oxalyl chloride (30.4 g, 0.24 mol) at 0° C., was added in a slow stream with stirring a solution of 2-methyl-1-penten-1-[N-pyrrolidinyl]-3-one 2 (L=N-pyrrolidino) (10.0 g, 60 mmol) in chloroform (10 ml) over a period of 20 minutes. The resulting solution was stirred at reflux for 30 minutes and then unreacted oxalyl chloride and solvent distilled from the reaction vessel to give a brown solid. Absolute ethanol (20 mls) was added cautiously to the reaction vessel at 0° C. via a reflux condenser and the resulting solution refluxed for 10 minutes. The reaction mixture was partitioned between diethyl ether (50 ml) and water (50 ml) and the aqueous phase basified to greater than pH 10 with 2M NaOH. The layers were separated and the organic phase washed with water (50 ml) and 2M HCl (2×50 ml). The ethereal layer was dried (anhydrous Na$_2$SO$_4$), filtered and evaporated to give a solid (11.6 g). The solid was dissolved in the minimum volume of hot petroleum ether (80–100°) and treated with activated charcoal (ca 5 g) for 5 minutes. After filtration through celite, the solution crystallised upon cooling to give 3 (R=Ethyl) (3.5 g). A second crop of 3 (R=Ethyl) (1.1 g) was obtained by concentration of the mother liquors to give a total yield of 3 (R=Ethyl) (4.6 g, 39%). m.pt. 86–87.5° C.; $^1$H-NMR (CDCl$_3$) δ 1.39 (t, J 7 Hz, 3H), 1.94 (s, 3H), 2.29 (s, 3H), 4.39 (q, J 7 Hz, 2H), 7.72 (s, 1H); Ms (APCI+) m/z (%) 197 (MH$^+$, 100).

Preparation of 3,5-Dimethyl-2-hydroxymethyl-4-pyrone 4.
Method A.

3,5-Dimethyl-2-methoxycarbonyl-4-pyrone 3 (R=Methyl) (294 mg, 1.62 mmol) and sodium borohydride (154 mg, 4.07 mmol) were dissolved in methanol (10 ml) and the resulting solution stirred at room temperature for 45 minutes. Silica gel (5 ml) was added and the solvent evaporated. The residue was applied to a pre-packed chromatography column assembled from silica gel (45 ml) in dichloromethane: ethyl acetate (1:1, v/v). Elution with firstly dichloromethane: ethyl acetate (1:1, v/v), then ethyl acetate, then methanol: ethyl acetate (1:3, v/v) gave 3,5-dimethyl-2-hydroxymethyl-4-pyrone 4 (230 mg, 92%) as a white solid. $^1$H-NMR (CDCl$_3$) δ 1.93 (s, 3H), 2.01 (s, 3H), 4.60 (s, 2H), 7.71 (s, 1H); selected IR (cm$^{-1}$, nujol) 3150–3500 (br, s), 1653 (s); Ms (APCI+) m/z (%) 155 (MH$^+$, 100).

Method B.

3,5-Dimethyl-2-ethoxycarbonyl-4-pyrone 3 (R=Ethyl) (1.04 g, 5.31 mmol) was dissolved in ethanol (10 ml) with brief warming then cooled to room temperature and stirred. Sodium borohydride (355 mg, 9.38 mmol) was added in one portion and the mixture stirred for three hours and then evaporated. The solution from concentrated hydrochloric acid (1 ml) in saturated brine (5 ml) was added and the resultant aqueous layer extracted with dichloromethane (3×50 ml). The combined organic extracts were dried (anhydrous Na$_2$SO$_4$), filtered and evaporated to give a residue (868 mg) which was dissolved in dichloromethane (5 ml) with gentle warming. Petroleum ether (15 ml, 80–100°) was added slowly, the resultant product filtered off and washed with petroleum ether (5 ml, 80–100°) to give 3,5-dimethyl-2-hydroxymethyl-4-pyrone 4 (675 mg, 83%). m.pt. 94.5–96° C.; $^1$H-NMR (CDCl$_3$) as before.

Preparation of 3,5-Dimethyl-2-hydroxymethyl-4-pyridone 5.

3,5-Dimethyl-2-hydroxymethyl-4-pyrone 4 (9.75 g, 63.3 mmol) was dissolved in 32% aqueous ammonia (0.880, 60 ml) in a 100 ml round bottom flask. The flask was sealed with a septum cap and made secure with wire. The solution was then stirred at 60° C. for 48 hours before being evaporated to dryness under reduced pressure to give 5 as an off-white solid (9.30 g, 60.8 mmol, 96% yield). Selected IR (cm$^{-1}$, nujol) 3150–3500 (br, s), 1639 (s); $^1$H-NMR (DMSO-d$_6$) δ 1.80 (s, 3H), 1.84 (s, 3H), 4.45 (s, 2H), 7.44 (s, 1H); Ms (APCI+) m/z (%) 154 (MH$^+$, 100).

Preparation of 4-Chloro-2-chloromethyl-3,5-dimethylpyridine 6. (X=Cl)

3,5-Dimethyl-2-hydroxymethyl-4-pyridone 5 (7.60 g, 49.7 mmol) was dissolved in phosphorus oxychloride (60 ml) and then stirred at reflux for 1 hour. The resulting solution was evaporated under reduced pressure and any remaining phosphorus oxychloride removed by evaporation from toluene. The residue was partitioned between chloroform (100m) and 2M NaOH (40 ml). The layers were separated and the aqueous layer back extracted with chloroform (3×50 ml). The combined chloroform layers were dried (anhydrous $Na_2SO_4$), filtered and evaporated to give a dark brown oil which was then redissolved in diethyl ether (100 ml), filtered and evaporated to give 6 (X=Cl) (8.28 g, 43.6 mmol, 88%). $^1$H-NMR (CDCl$_3$) δ 2.35 (s, 3H), 2.48 (s, 3H), 4.70 (s, 2H), 8.24 (s, 1H); Ms (APCI+) m/z (%) 190 ($^{35}$Cl$_2$-MH$^+$, 50).

Preparation of 2-[2-(4-chloro-3,5-dimethylpyridyl)methylthio]-5-methoxy-benzimidazole 7. (X=Cl)

4-Chloro-2-chloromethyl-3,5-dimethylpyridine 6 (X=Cl) (8.28 g, 43.6 mmol) and 5-methoxy-2-mercaptobenzimidazole (7.84 g, 43.5 mmol) were dissolved in tetrahydrofuran (150 ml) and 2M NaOH (60 ml) added. The resulting solution was warmed with stirring at 40° C. for 18 hours and then partitioned between dichloromethane (150 ml) and water (150 ml). The layers were separated and the aqueous layer back extracted with dichloromethane (3×50 ml). The combined organic layers were dried (anhydrous $Na_2SO_4$), filtered and evaporated to give 7 (X=Cl) as a thick colourless oil (13.98 g, 41.9 mmol, 96% yield). $^1$H-NMR (CDCl$_3$) δ 2.34 (s, 3H), 2.43 (s, 3H), 3.81 (s, 3H), 4.46 (s, 2H), 6.81 (dd, J 8.5 and 2 Hz, 1H), 7.00 (d, J 2 Hz, 1H), 7.39 (d, J 8.5 Hz, 1H), 8.25 (s, 1H); Ms (APCI+) m/z (%) 334 ($^{35}$Cl-MH$^+$, 100).

Preparation of 2-[2-(3,5-dimethyl-4-methoxypyridyl)methylthio]-5-methoxy-benzimidazole 8.

Powdered potassium hydroxide (14.45 g, 97%, 250 mmol) was suspended in dimethyl sulphoxide (90 g) containing methanol (8.16 g, 255 mmol) and the resulting mixture stirred at 70° C. for 30 minutes. 2-[2-(4-chloro-3,5-dimethylpyridyl)methylthio]-5-methoxy-benzimidazole 7 (X=Cl) (12.88 g, 38.6 mmol) in dimethyl sulphoxide (20 g) was added in one portion and the resulting mixture stirred at 70° C. for 24 hours. The majority of the solvent was removed by vacuum distillation and the residue partitioned between water (100 ml) and chloroform (100 ml). The layers were separated and the aqueous layer back extracted with chloroform (2×50 ml). The combined chloroform extracts were dried (anhydrous $Na_2SO_4$), filtered and evaporated to give 8 as a thick colourless oil (10.49 g) containing approximately 10% by weight DMSO. $^1$H-NMR (CDCl$_3$) δ 2.26 (s, 3H), 2.30 (s, 3H), 3.76 (s, 3H), 3.82 (s, 3H), 4.37 (s, 2H), 6.81 (dd, J 8.5 and 2.5 Hz, 1H), 6.9–7.5 (br, 2H), 8.24 (s,1H); Ms (APCI+) m/z (%) 330 (MH$^+$, 100).

Preparation of 2-[2-(3,5-dimethyl-4-methoxypyridyl)methylthio]-5-methoxy-benzimidazole hydrochloride 9.

Crude 2-[2-(3,5-dimethyl-4-methoxypyridyl)methylthio]-5-methoxy-benzimidazole 8 (10.25 g equivalent to approx. 9.23 g of pure 8) was dissolved in methanol (29.1 ml) containing hydrogen chloride (29.1 mmol). Ethyl acetate (29.1 ml) was added slowly to the solution and the hydrochloride salt crystallised. The product was filtered off and washed with methanol/ethyl acetate (1:1 v/v, 2×20 ml) to give a white solid (6.81 g). Concentration of the mother liquors resulted in a second crop of product (1.91 g). Total yield of hydrochloride salt 9 (8.72 g, 23.9 mmol, 85% yield). m. pt. 154–6° C.; $^1$H-NMR (DMSO-d$_6$) δ 2.28 (s, 3H), 2.31 (s, 3H), 3.80 (s, 3H), 3.87 (s, 3H), 4.91 (s, 2H), 6.93 (dd, J 9 and 2 Hz, 1H), 7.07 (d, J 2 Hz, 1H), 7.49(d, J 9, 1H), 8.40 (s,1H); Ms (APCI+) m/z (%) 330 (MH$^+$-HCl, 100).

Preparation of Omeprazole 10.

To powdered potassium hydroxide pellets (2.48 g, 97%, 42.9 mmol) in dimethyl sulphoxide (19 g) was added methanol (1.40 g, 43.8 mmol) and the mixture stirred at 70° C. for 30 minutes. 2-[2-(4-chloro-3,5-dimethylpyridyl)methylthio]-5-methoxy-benzimidazole 7 (X=Cl) (2.33 g, 7.0 mmol) was added in one portion and the resulting mixture stirred at 70° C. for 16 hours. The mixture was concentrated by distillation (70° C., ca. 0.3 mmHg) of solvent (13.5 g) then added to water (40 ml) and dichloromethane (60 ml). The aqueous phase was separated, re-extracted with chloroform (3×60 ml), the four organic layers combined, dried (anhydrous $Na_2SO_4$), filtered and evaporated to give crude 2-[2-(3,5-dimethyl-4-methoxypyridyl)methylthio]-5-methoxy-benzimidazole 8 (2.09 g, approx. 80% by weight, major impurity residual dimethyl sulphoxide). Dichloromethane (50 ml), was added and the resulting solution cooled to −10° C. with stirring. Metachloroperoxy-benzoic acid (1.01 g, 87%, 5.1 mmol) was added and the mixture stirred at −10° C. for 20 minutes. The solution from sodium hydrogen carbonate (20 g) and sodium thiosulphate (10 g) in water (100 ml) was added and the mixture stirred to room temperature over 30 minutes. The aqueous layer was separated, re-extracted with dichloromethane (2×70 ml), the three organic layers combined, dried (anhydrous $Na_2SO_4$), filtered and evaporated to give crude omeprazole (1.975 g). This was dissolved in dichloromethane (4 ml) with gentle warming at 40° C. then diethyl ether (8 ml) was added dropwise and the mixture cooled to 5° C. for 30 minutes. The product was collected by filtration, washed with dichloromethane: diethyl ether (1:2, v/v, 3 ml) then diethyl ether (3 ml) to give omeprazole 10 (1.46 g, 4.23 mmol, 60% from 7) (X=Cl). m.pt. 153–5° C.; $^1$H-NMR (CDCl$_3$) δ 2.13 (s, 3H), 2.22 (s, 3H), 3.61 (s, 3H), 3.84 (s, 3H), 4.75 (s, 2H), 6.8–7.8 (br x 3, 2H), 6.94 (dd, J 9 and 2 Hz, 1H), 8.21 (s, 1H), 12.30 (br, 1H).

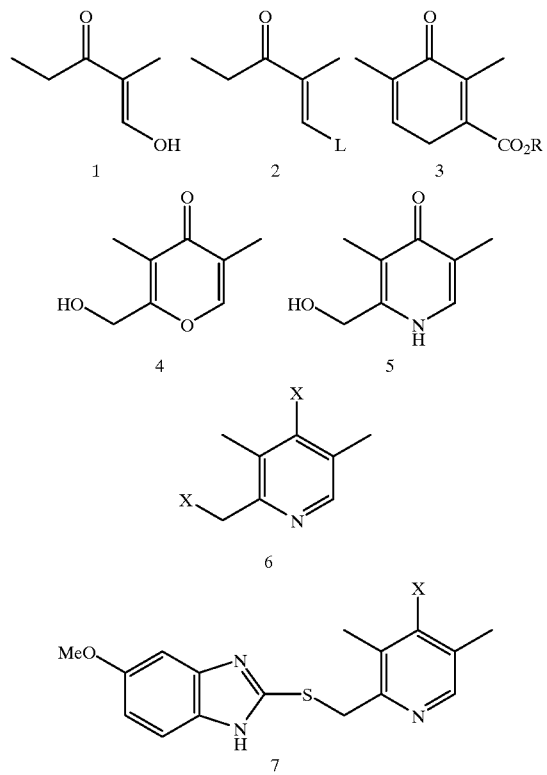

-continued

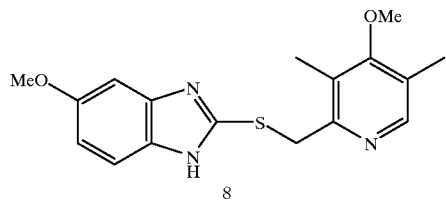

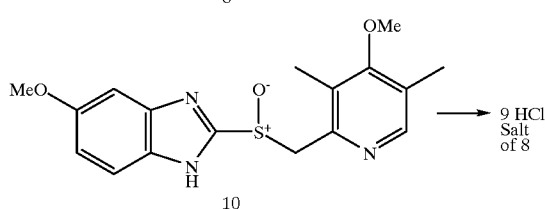

We claim:
1. A compound having the formula:

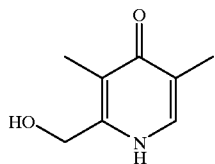

2. A method of making a compound of claim 1

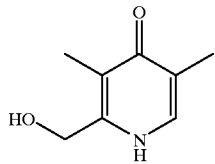

which method comprises reacting a compound of the formula

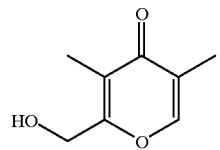

with ammonia.

3. A method of using the compound of claim 1 in making a compound of the formula,

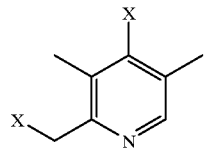

where X is chloro or bromo, which method comprises reacting a compound of the formula

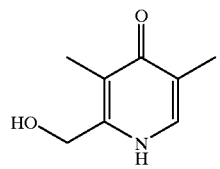

with a chlorinating or brominating agent.

4. A method as claimed in claim 3, wherein there is used a chlorinating or brominating agent selected from one or more of phosphorus oxychloride, phosphorus pentachloride, triphenylphosphine dichloride, triphenylphosphine dibromide, triphenylphosphite dichloride, triphenylphosphite dibromide, phosphorus tribromide and thionyl chloride.

* * * * *